US 6,733,290 B2

(12) United States Patent
West et al.

(10) Patent No.: US 6,733,290 B2
(45) Date of Patent: May 11, 2004

(54) DENTAL ILLUMINATION DEVICE

(76) Inventors: John West, 183 Moore La., Antoyo Grande, CA (US) 93420; Scott Ganaja, 1232 Descanso Dr., San Luis Obispo, CA (US) 93405

( * ) Notice: Subject to any disclaimer, the term of this patent is extended or adjusted under 35 U.S.C. 154(b) by 0 days.

(21) Appl. No.: 10/229,386

(22) Filed: Aug. 28, 2002

(65) Prior Publication Data
US 2003/0091954 A1 May 15, 2003

Related U.S. Application Data
(60) Provisional application No. 60/315,022, filed on Aug. 28, 2001.

(51) Int. Cl.⁷ .............................. A61C 1/00; A61C 5/00
(52) U.S. Cl. .......................................... 433/29; 433/215
(58) Field of Search .......................... 433/29, 32, 215; 606/14, 17; 600/241, 245

(56) References Cited

U.S. PATENT DOCUMENTS

| 4,144,882 A | * | 3/1979 | Takemoto et al. |
| 5,487,662 A | * | 1/1996 | Kipke et al. ................ 433/37 |
| 5,800,165 A | | 9/1998 | Kirsch et al. |
| 5,813,854 A | | 9/1998 | Nikodem |
| 6,077,073 A | | 6/2000 | Jacob |
| 6,162,055 A | * | 12/2000 | Montgomery et al. ...... 433/216 |
| D438,622 S | | 3/2001 | Chang |
| 6,254,388 B1 | | 7/2001 | Yarborough |
| 2003/0036037 A1 | * | 2/2003 | Zavitsanos et al. ......... 433/215 |

* cited by examiner

Primary Examiner—Cary E. O'Connor
(74) Attorney, Agent, or Firm—John W. Ryan; Dechert, LLP

(57) ABSTRACT

An electromagnetic radiation conveyance device comprising a proximal end, a distal end, and a light directing intermediate portion. The proximal end is configured for attachment to an electromagnetic radiation emitting device. The distal end is anatomically preformed with a profile complementary to a shape of a dental arch. The light directing intermediate portion is between the proximal end and the distal end. In addition, the light directing intermediate portion is configured to convey electromagnetic radiation from the proximal end to the distal end.

21 Claims, 4 Drawing Sheets ns. Similarly, the combination of light and oxygen radical generating agents has provided a more effective means for whitening teeth. In view of the use of photoinitiators in dental restorative compositions and the use of light activated bleaching agents, there has been a strong push to improve the light sources that provide the light for curing dental restorative compositions and for the activation of bleaching agents that are applied during teeth whitening procedures.

DENTAL ILLUMINATION DEVICE

REFERENCE TO RELATED APPLICATION

This application claims the benefit of U.S. Provisional Application No. 60/315,022, filed Aug. 28, 2001, which is hereby incorporated by reference.

FIELD OF THE INVENTION

The present invention relates generally to a device that attaches to a standard light source to transmit and distribute light energy simultaneously across the arches of upper and lower teeth for dental tooth whitening and photo initiation of light curing resins while at the same time retaining the benefits of the light source to be used for individual tooth whitening and curing. More particularly, the invention may use a single standard light source to simplify the process of tooth whitening and curing.

BACKGROUND OF THE INVENTION

As the world population increases and dental hygiene becomes more important, there are and will be a substantial increase in the number of patient visits to the dentist office. The needs from one patient to another may vary from teeth cleaning to taking x-rays, from filling cavities to whitening teeth. With an increasing number of visits to the dentist office, dentists face a daunting task of not only increasing their patient loads, but also providing a more effective and efficient patient care.

There have been many advances in dentistry over the years which have improved patient care. One of the advances includes the incorporation of photoinitiators into adhesive compositions useful for dental restoration. The light-initiated curing of a polymerizable matrix material involves photosensitization of light-sensitive compounds by ultraviolet or visible light, which, in turn, initiates polymerization of the matrix material. The photoinitiators are well known, and include by way of example, the combination of a photosensitive ketone (an acceptor in exciplexes) and a tertiary amine (a donor in exciplexes). Typical photosensitive ketones include benzophenone, acetophenone, thioxanthen-9-one, 9-fluorenone, anthraquinone, 4'-methoxyacetophenone, diethoxyacetophenone, biacetyl, 2,3-pentadione, benzyl, 4,4'-methoxybenzil, 4,4'-oxidibenzil, and 2,3-bornadione (dl camphroquinone). Typical tertiary amines include ethyl-4-dimethyl amino benzoate, ethyl-2-dimethyl amino benzoate, 4,4-bis (dimethylamino) benzophenone, methyldiethanolamine, and dimethylaminobenzaldehyde.

Another advance in the dental arts is the ability to bleach teeth back to the original white color. This, coupled with society's consciousness of teeth discoloration has resulted in the demand for oral care products and associated procedures for whitening teeth to rapidly increase. There are many methods of treatment relating to the bleaching of teeth. Power bleaching materials contain high concentrations of hydrogen peroxide or other source of active oxygen. Most dental bleaches are applied as gels or pastes which are freshly prepared as needed in the particular dental office. Since hydrogen peroxide is a liquid, a powder is mixed with it for thickening. There may also be other ingredients present, such as catalysts or indicators. Often times, light or heat is part of power bleaching. One of the most frequently used procedures is the application of bleaching agents, such as hydrogen peroxide, and light to whiten discolored teeth.

The combination of photoinitiators and light has rapidly lowered the curing time while increasing bonding strengths The light sources currently in use fall into two categories, single point sources and multiple point sources. Single point sources transmit light to a single spot through a single optic while multiple point sources transmit light with multiple transmitting optics. Both systems rely on rigid light guides, flexible liquid light guides, and fiber optic bundles to transmit a spot of light at the distal end of the optics. The size of the spot is dependant on the construction of the optic and the active diameter of transmitting optic. Typical light sources include but are not limited to Tungsten Halogen Lamps and derivatives of this technology, Xenon Short Arc Lamps, Metal Halide Lamps, Laser, and LED's.

Despite the plethora of light sources, existing technology that provides two arch illumination fails to provide a method or make it easy for the clinician to work on a single tooth. A drawback to these existing full arch light sources that are used to transmit light simultaneously to upper and lower teeth is that they are large, bulky and cumbersome thus requiring a dedicated office. Moreover, these light sources are not easily transportable. These instruments take up floor space and cannot be mounted to the dental chair, wall or counter top. Furthermore, the optic device that transmits the light is not disposable and cannot be easily sterilized.

The full arch light sources are limited to two arch illumination and cannot be used to individually treat discoloration of a single tooth. A further drawback to this equipment is that it is limited to one type of procedure (i.e., exposure of multiple teeth with light). In other words, the equipment does not allow for the exposure of a single spot such as one tooth or one specific area of a tooth. Even though a clinician may only be treating one tooth, the current technologies expose multiple teeth. This is inefficient since a patient's teeth may have varied coloration (e.g., stained) and thus the exposure of all the teeth will not allow the clinician to resolve the single discolored tooth that is being treated.

Today's equipment relies on multiple light transmitting devices such as liquid light guides or fiber optic bundles to focus the light energy around the arches of the teeth. Currently, single point light sources do not allow simultaneous two arch illumination. In contrast to the multiple point sources, the existing single point light sources transmit light to a spot that is roughly the size of a tooth. Thus, the single point light sources cannot be used to treat both arches simultaneously.

U.S. Pat. No. 5,813,854 ("the '854 patent"), attempts to remedy the shortcoming of the existing technologies. The '854 patent discloses a device that utilizes a light diffusion system to direct light to all of the patients tooth. The '854 patent device includes light diffusion means that must be installed in the structure of the device. The light diffusion means are installed in a housing and are used for diffusing light directed into the housing throughout the housing. This complicated system has several drawbacks including the required insertion of diffusion means such as optical gratings (i.e., mirrors) which extend between the upper and lower surfaces of the device. These gratings comprise a complex system of multiple mirrors to reflect light inside the housing to the front of the housing and to the patient's mouth. In addition, the diffusion of light is not efficient because light scatters in directions that are not useful.

A further drawback of the above-mentioned patented device is that it is an elaborate, cumbersome and expensive device. This complex diffusing means requires additional machining and manufacturing protocols which drive the costs of the device higher. It employs a number of components which makes it inherently less reliable than a device that is a simple one component structure.

SUMMARY OF THE INVENTION

One embodiment of the present invention pertains to an electromagnetic radiation conveyance device. This electromagnetic radiation conveyance device includes a proximal end, a distal end, and a light directing means. The proximal end is configured for attachment to an electromagnetic radiation emitting device. The distal end is anatomically preformed with a profile complementary to a shape of a dental arch. The light directing means is intermediate between the proximal end and the distal end. In addition, the light directing means is configured to convey electromagnetic radiation from the proximal end to the distal end.

Another embodiment of the present invention relates to a method of whitening at least one tooth in a dental arch. In this method, a whitening solution is applied to at least one tooth. The whitening solution is photoreactive. In this regard, whitening action of the whitening solution is increased in response to absorption of electromagnetic radiation. Additionally, in this method, electromagnetic radiation is applied to the dental arch utilizing an illumination system. This illumination system includes an electromagnetic radiation emitting device and an electromagnetic radiation conveyance device. The electromagnetic radiation emitting device includes a receptacle and the electromagnetic radiation emitting device is configured to emit electromagnetic radiation from the receptacle. The electromagnetic radiation conveyance device includes a proximal end, a distal end, and a light directing means. The proximal end is configured for attachment to the receptacle. The distal end is anatomically preformed with a profile complementary to a shape of a dental arch. The light directing means is intermediate between the proximal end and the distal end. In this regard, the light directing means is configured to convey electromagnetic radiation from the proximal end to the distal end.

DETAILED DESCRIPTION OF AN EMBODIMENT OF THE INVENTION

Figure 1:
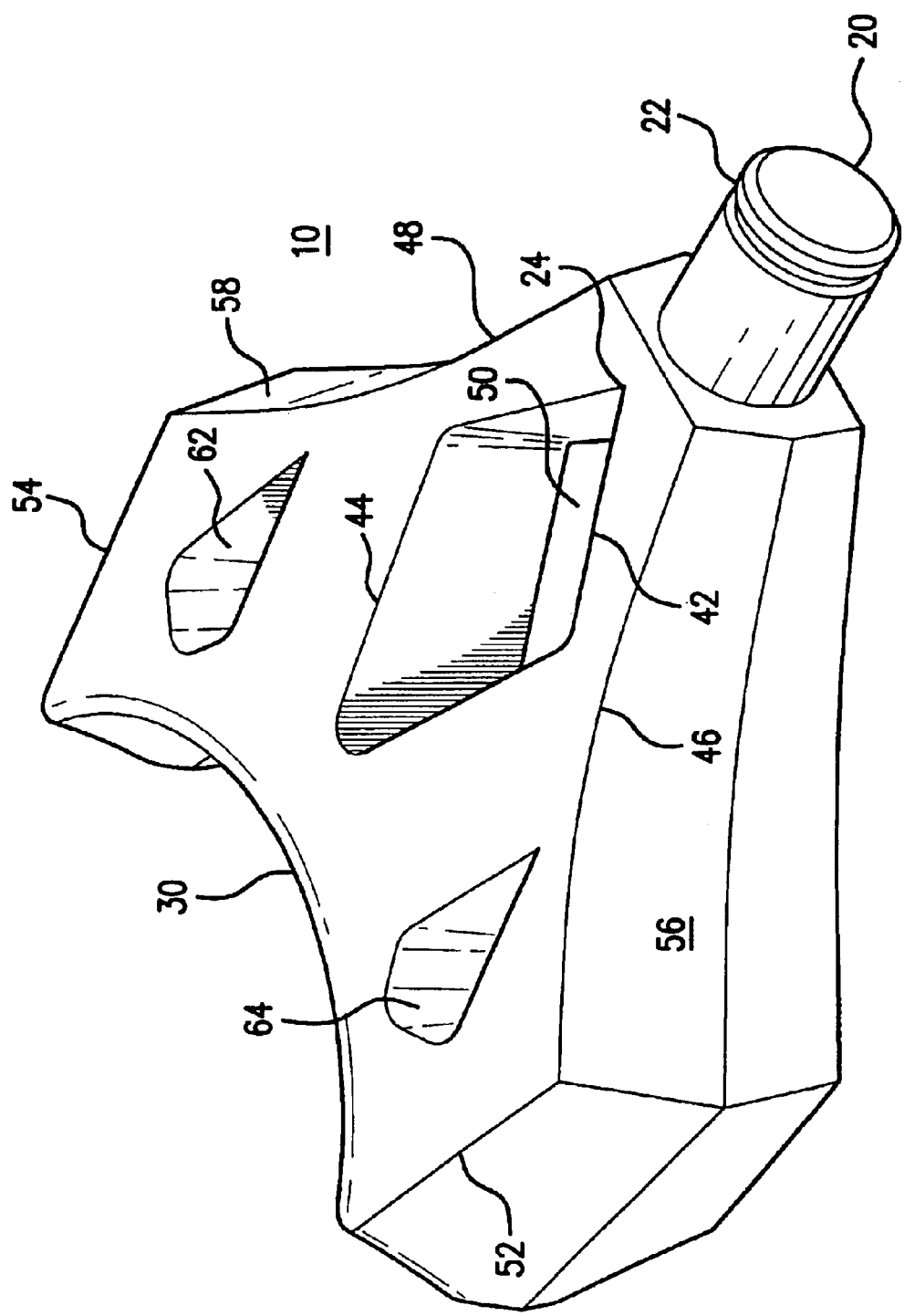
FIG. 1 is a perspective view of an illuminating device of the present invention.
Figure 2:
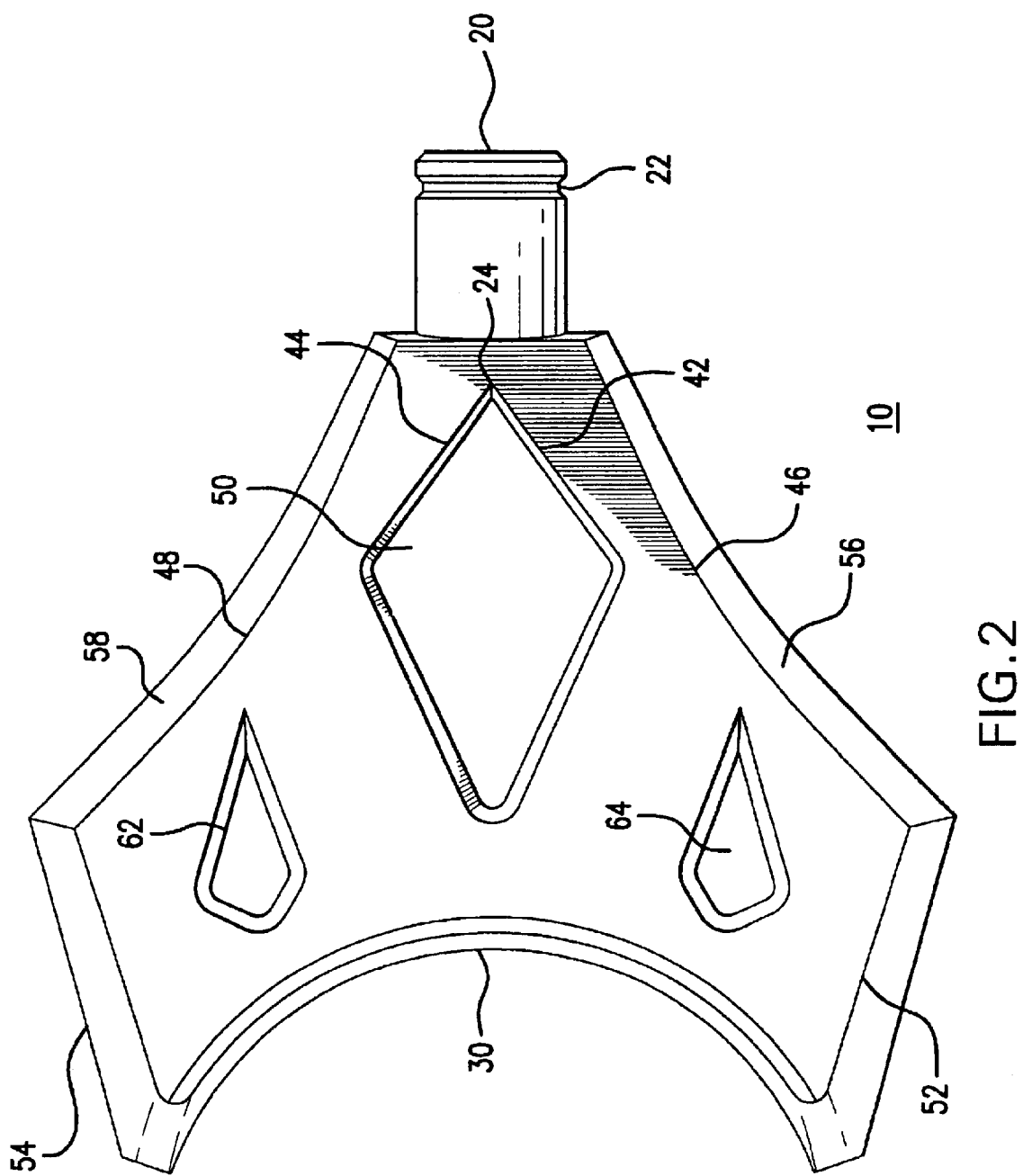
FIG. 2 is a side elevation view of the present invention.

The present invention is capable of single or multiple teeth bleaching and curing. Similarly, the present invention allows clinician to treat one or two arches, or single teeth all with the same light source. With reference to FIGS. 1–2, there is a dental device 10 of the instant invention particularly adapted to perform a bleaching method and curing method of the instant invention. Device 10 is disposable and allows a standard single point light source that is lightweight and portable to be used for two arch illumination as well as the treatment of individual teeth. The term "light" is not meant to limit the invention to infrared, visible, and/or ultraviolet forms of light, but rather, the invention may utilize any portion of the electromagnetic spectrum. The body of dental device 10 is a simple one-piece article of manufacture. The single piece construction is molded, cast, or machined from a transparent material. Preferably, the construction is molded. The material of device 10 preferably has high transmittance characteristics. Examples of the material include, but are not limited to, acrylic, glass, polycarbonate, and polystyrene. Preferably, the material is acrylic. Furthermore, it is to be understood that the transparency of the material is with respect to the frequency of electromagnetic radiation being transmitted. Generally, the electromagnetic spectrum is defined as being between a frequency range of approximately $10^{23}$ hertz to 0 hertz. However, different dental formulations utilized in dental procedures may be influenced (e.g., polymerized and the like) by a subset of the electromagnetic spectrum. Therefore, it is within the scope of the invention that the materials used to construct device 10 is transparent to a subset of the electromagnetic spectrum. Similarly, the transparency of the material utilized to construct device 10 may be dependent upon the dental formulation used.

The dimensions of device 10 can vary as long as it allows for the clinician to effectively and simultaneously illuminate the upper and lower tooth arches of a dental patient. Preferably, device 10 is configured and dimensioned such that the curvature and height of device 10 closely matches the arch of the patient's upper and lower teeth. In this regard, a distal end 30 of the device 10 may be anatomically preformed with a profile complementary to a shape of an average dental arch of a statistically pre-determined set of individuals. In addition, other sizes may be used for smaller and larger patient mouths.

In an embodiment of the invention, the device 10 is configured to direct light (e.g., light directing device, light directing means, etc.). In this regard, when electromagnetic radiation (e.g., light) is transmitted (e.g., conveyed, directed, etc.) through device 10 from the proximal (input) end 20 to the distal (output) end 30, the light distribution is controlled so that it is projected simultaneously and evenly across the entire upper and lower tooth surfaces. When dental procedures require tooth whitening solutions or light cure resin formulations to be placed on one or multiple teeth, and where it is possible to simultaneously treat all of these teeth, device 10 can be positioned adjacent to the upper and lower tooth arches and light exposure can be projected onto the patients teeth. In addition, it is shown that distal end 30 of device 10 is configured and dimensioned to cover the upper and lower arches of a patient's mouth.

In order to achieve the illumination of the patient's teeth, device 10 can be attached to an electronic control device (i.e., standard light source). Device 10 has a proximal end 20 formed to attach directly into the light guides and receptacles found on standard light sources. The use of this device 10 on standard light sources shall not preclude or alter the light source for other intended purposes. Proximal end 20 of the device 10 can be in any shape that allows for the transmittance of light through device 10 and towards a patient's teeth. Particularly, proximal end 20 will be in the shape that fits into any electronic control device receptacle. This can be achieved simply by changing the size and the diameter of proximal end 20.

Preferably, proximal end 20 is provided with a groove 22 that is included along the circumference of proximal end 20.

Groove 22 allows device 10 to attach to an electronic control device or the like. Particularly, groove 22 is configured and dimensioned with sufficient rigidity to allow it to be inserted through an opening or attached to any number of standard light sources. For example, proximal end 20 is configured to attach to Den-Mat's electronic control device, the Rembrandt Sapphire Plasma Arc Light Pistol Hand Piece. The dimensions of proximal end 20 can be modified to fit any light source available in the field. Given its adaptability, device 10 can even be used with or without a pistol hand piece.

Once the light enters the proximal end 20, the light is directed immediately to the left or right hand side of device 10, via corner (or also called a splitter) 24. Corner 24 is the leading edge of a hollow core 50 of device 10. The light then continues and reflects off the inner walls 42 and 44, respectively, on either the left or the right side of device 10. This brings light towards the patient's teeth from the sides (right and left), for a more useful light distribution, filling the crevices with light and reducing shadows. Then the light turns back in and may reflect off one or more walls, and eventually makes its way towards the distal end 30 of device 10. Thus, light entering the proximal end 20 is directed in a manner such that it exits the distal end 30. As such, this system actually directs light to the patient's teeth primarily from the sides as well as from several other (secondary) directions as opposed to a diffusion system.

One embodiment of device 10 comprises a core 50 that is strategically placed in front of proximal end 20 such that the incoming light is reflected toward the left or right hand side of device 10. The angle of the core angle, via corner 24, is about 45°. The angle of corner 24 is measured from the center line or center ray of light in FIG. 3. At this particular angle, the light reflects from inner walls 42 and 44, respectively, rather than going through the walls of device 10. If the angle is greater than about 47° from the center line, the light will pass through inner walls 42 and 44. Thus, if the angle is less than about 47°, the light will reflect off of inner walls 42 and 44, respectively, towards the front of device 10.

Corner 24 and inner walls 42 and 44 are geometrically and optically oriented to provide the best throughput and distribution of the source light from the proximal end 20 to the distal surface 30. The geometric design provides a fluid pathway for the light by way of reflection against inner walls 42 and 44 of device 10, the light pattern extends out from the distal end 30 and surrounds each tooth surface that is illuminated. The outer surface walls 56 and 58 on the outside of device 10 can be straight or curved, depending on the best manufacturing method. The angling of inner walls 42 and 44 keep the light from leaking out the side of device 10. As a result, when light is proceeding through device 10, the entire device 10 does not glow because light is not leaking out of device 10. Rather, the rays of light are being reflected towards the front (distal end) so that only the front part of device 10 glows.

Outer walls 46 and 48, respectively, on either the left and the right side of device 10 reflect the light back towards the center of device 10. Outer walls 46 and 48 can be straight or curved. A curved surface spreads out the light out over more area. Alternatively, a straight line provides a more concentrated light stream. Preferably, outer walls 46 and 48 are straight. Similarly, further outer walls 52 and 54 respectively, reflect (e.g., direct) the light out towards the distal end 30. This is illustrated in more detail in FIG. 3.

Another embodiment of the invention includes additional cores, 62 and 64. Cores 62 and 64 are incorporated into device 10 so that they have a minimum impact of device 10, and to minimize the wall thickness of device 10 for engineering purposes. The nominal wall thickness makes device 10 easier to mold. A preferred shape of cores 62 and 64 is in the form of a teardrop. Cores 62 and 64 are positioned so that they have a minimal impact on the light output and direction. However, any shape can be used that does not significantly effect the direction or intensity of the light as it travels to the surface of the distal end 30.

Figure 3:
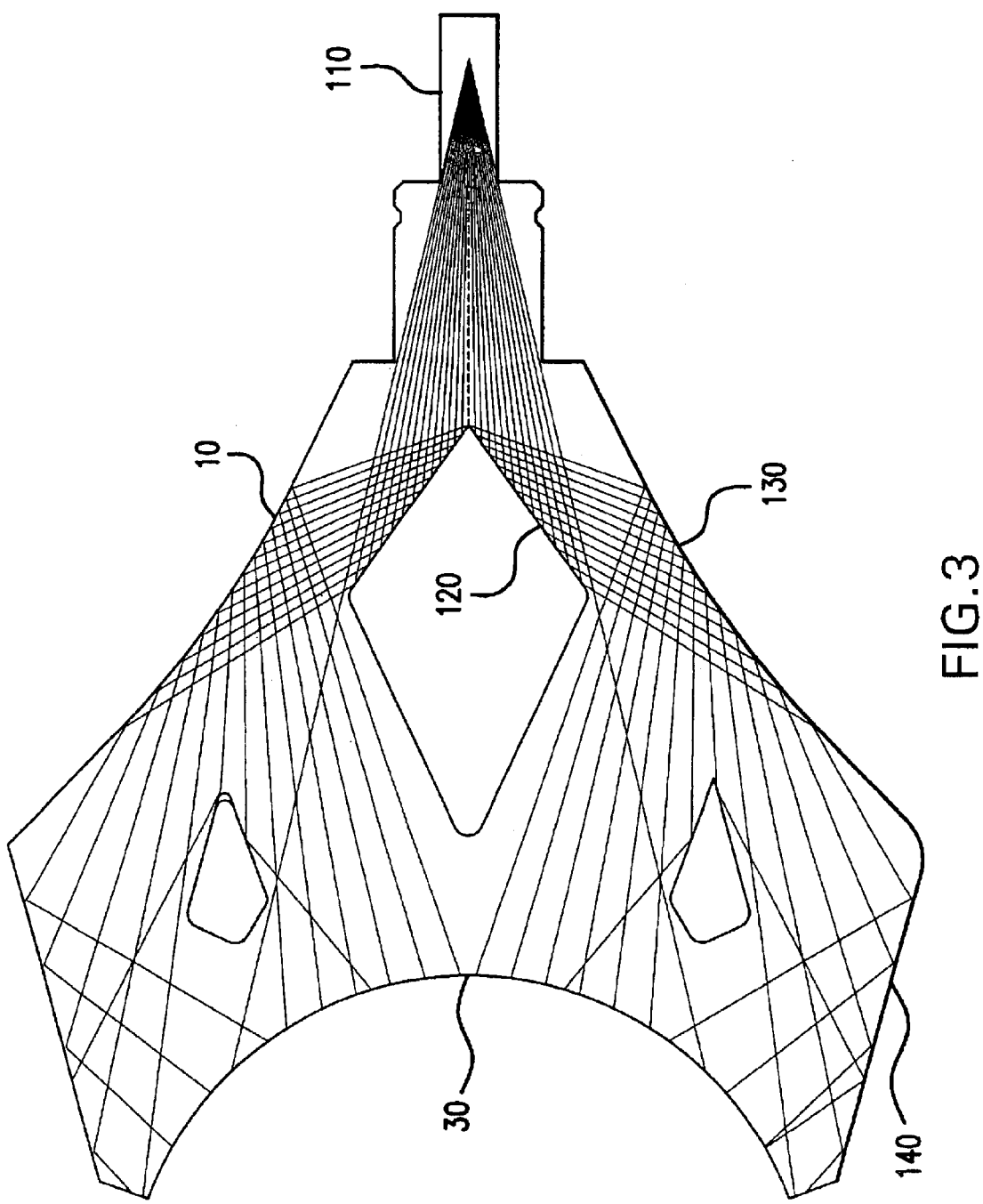
FIG. 3 is a top plan view of the light pathway through the present invention.

With reference to FIG. 3, there is shown a "ray trace." This "ray trace" demonstrates the pathway of light from a light source 110 through an embodiment of device 10. Particularly, it shows the origination of the light from a light source 110, then as the light proceeds through device 10, a majority of the light hits wall 120 and then bounces to wall 130. After hitting wall 130, most of the light will proceed to the distal end 30 of device 10 and project onto the patient's teeth from several directions.

It is recognized that not all of the light will follow the aforementioned path. For example, some light may proceed directly from light source 110 through device 10, proceed to the distal end 30 of device 10 and project onto the patients teeth.

Furthermore, some light may proceed from light source 110, hit wall 120 and then bounces to wall 130. After reflecting form wall 130, the light proceeds to hit wall 140 and then exits out of distal end 30 of device 10 and projects onto the patient's teeth.

An advantage with device 10 over other devices is that the light intensity is controlled by the light source itself. The higher the amount of energy delivered by the light source, the better the intensity of light directed at the patient's teeth. In one successful test, the light source transmitted over 1 watt of power out the end of the light guide into the device. Both higher and lower power lights can interface with device 10. Since the lights dictate the intensity of the light, the effectiveness of device 10 will depend on the light power used in conjunction with device 10.

It should be recognized that the aforementioned examples are for illustration purposes, and as one of ordinary skill in the art can see, there are number of different pathways the light can follow on its path through device 10. Indeed, although there are a myriad of pathways, the light still proceeds to the distal end 30 of device 10 and is projected onto the patient's teeth.

Figure 4:
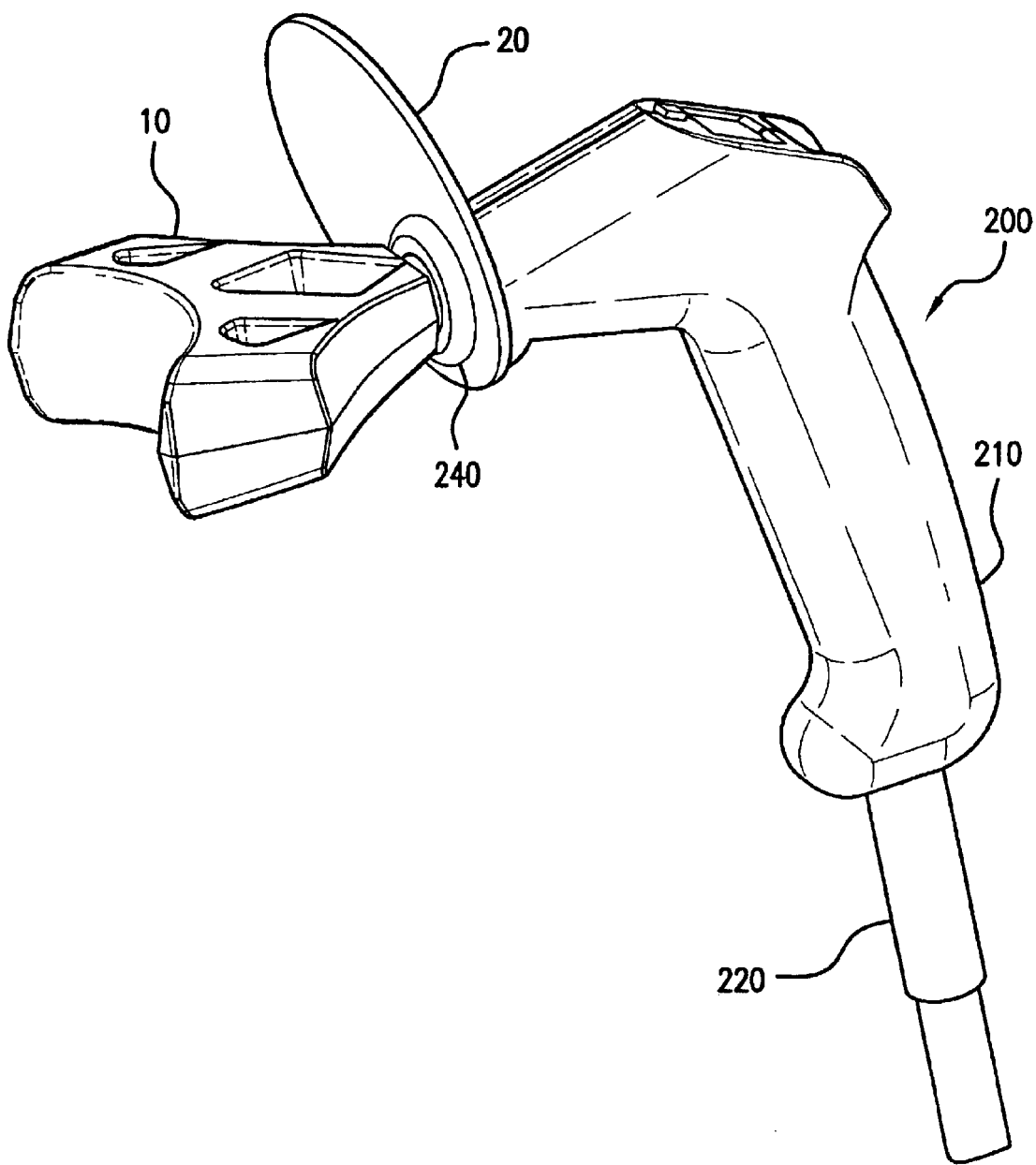
FIG. 4 is a side elevation view of the present invention attached to an electronic control device.

As shown in FIG. 4, for example, proximal end 20 is configured to plug into a single point light source and allows for the simultaneous illumination of both arches. Proximal end 20 can also be configured to a multiple point light source. Similarly, if the clinician desires to treat a single spot on a tooth, the device 10 can easily be removed from the electronic control device 200. This allows the clinician to reinsert a standard dental probe. The flexibility of inserting and removing device 10, allows the clinician to use the same light source regardless of the number of teeth being treated.

FIG. 4 demonstrates how device 10 is connected to a standard electronic control device 200 that is typical in the field. The electronic control device 200 holds device 10 in place such that the clinician doesn't have to hold device 10, rather the clinician can hold the electronic control device 200 for better handling while bleaching or curing the patient's teeth. When device 10 is used for bleaching or curing, there is an arm 210 which would hold the electronic control device 200 in a position in front of the patient's mouth. Connected to electronic control device 200 can be any standard light source 220. A particularly preferred electronic control device 200 is the Den-Mat electronic control device, the Rembrandt Sapphire Plasma Arc Light Pistol Hand Piece. However, it is recognized that any electronic control device 200 can be utilized with this invention. For example, electronic control device 200 may include any suitable device configured to emit light within a suitable frequency range. In order to attach device 10 to the electronic control device 200, the clinician can remove a probe 100, if already contained in electronic control device 200, and then attach device (i.e., bleaching illuminator) 10 into the same receptacle 240 of the electronic control device 200.

In an embodiment of the present invention, the electronic control device 200 may be attached to device 10 to form an illumination system for dental procedures such as, bleaching, curing, and the like. For example, the clinician may perform a bleaching procedure in the following illustrative manner. A photoreactive whitening solution may be applied to one or more of a patient's teeth. In this regard, whitening action of the whitening solution is increased in response to absorption of electromagnetic radiation. Additionally, the distal end 30 may be positioned near the patient's mouth and electromagnetic radiation may be applied to the dental arch utilizing the illumination system. Furthermore, it is to be understood that it is within the scope of the invention to position the control device 200 within the device 10. In this regard, optical components such as, Xenon Short Arc Lamps, Metal Halide Lamps, Laser, LED's and the like may be incorporated into the proximal end 20 of the device 10.

While the preferred embodiments of the invention have been particularly described in the specification and illustrated in the drawing, it should be understood that the invention is not so limited. Many modifications, equivalents, and adaptations of the invention will become apparent to those skilled in the art without departing from the spirit and scope of the invention as defined in the appended claims. For example, device 10, or variations of device 10 that may include modifications to the original shape and the inclusion of optical components, may be used for, but not limited to, tooth whitening, direct and indirect bonding of orthodontic brackets, bonding porcelain laminates, gingival tissue protection, and direct and indirect curing of composites and bonding adhesives.

What is claimed is:

1. An electromagnetic radiation conveyance device comprising:
   a proximal end configured for attachment to an electromagnetic radiation emitting device;
   a distal end anatomically preformed with a profile complementary to a shape of a dental arch; and
   a light directing means comprising a core, a left side, and a right side, wherein said light directing means is intermediate between said proximal end and said distal end, wherein said light directing means is configured to convey electromagnetic radiation from said proximal end to said distal end.

2. The electromagnetic radiation conveyance device according to claim 1, wherein said electromagnetic radiation emitting device is positioned within said proximal end.

3. The electromagnetic conveyance device according to claim 1, constructed from a transparent material.

4. The electromagnetic radiation conveyance device according to claim 3, constructed from at least one of acrylic, glass, polycarbonate, and polystyrene.

5. The electromagnetic radiation conveyance device according to claim 1, wherein said core having a first angle of approximately 45°, wherein said core is configured to substantially reflect electromagnetic radiation toward said left side and said right side.

6. A system to transmit electromagnetic radiation to a dental arch, said system comprising:
   an electromagnetic radiation emitting device having a receptacle, wherein said electromagnetic radiation emitting device is configured to emit electromagnetic radiation from said receptacle; and
   an electromagnetic radiation conveyance device comprising:
   a proximal end configured for attachment to said receptacle;
   a distal and anatomically preformed with a profile complementary to the shape of a dental arch; and
   a light directing means comprising a core, a left side, and a right side,
   wherein said light directing means is intermediate between said proximal end and said distal end, wherein said light directing means is configured to convey electromagnetic radiation from said proximal end to said distal end.

7. The system according to claim 6, wherein said proximal end is placed into a receptacle in close proximity to the distal end of the radiation emitting device.

8. The system according to claim 6, wherein said electromagnetic radiation conveyance device is constructed from a transparent material.

9. The system according to claim 8, wherein said electromagnetic radiation conveyance device is constructed from at least one of acrylic, glass, polycarbonate, and polystyrene.

10. The system according to claim 6, wherein said core having a first angle of approximately 45°, wherein said core is configured to reflect electromagnetic radiation toward said left side and said right side.

11. A method of whitening at least one tooth in a dental arch comprising:
    applying whitening solution to at least one tooth, said whitening solution is photoreactive, wherein whitening action of said whitening solution is increased in response to absorption of electromagnetic radiation; and
    applying electromagnetic radiation to said dental arch utilizing an illumination system comprising:
    an electromagnetic radiation emitting device having a receptacle, wherein said electromagnetic radiation emitting device is configured to emit electromagnetic radiation from said receptacle; and
    an electromagnetic radiation conveyance device comprising:
    a proximal end configured for attachment to said receptacle;
    a distal end anatomically preformed with a profile complementary to the shape of a dental arch; and
    a light directing means comprising a core, a left side, and a right side, wherein said light directing means is intermediate between said proximal end and said distal end, wherein said light directing means is configured to convey electromagnetic radiation from said proximal end to said distal end.

12. The method according to claim 11, wherein electromagnetic radiation is applied utilizing said illumination system having said electromagnetic radiation emitting device is positioned within said proximal end.

13. The electromagnetic conveyance device according to claim 11, wherein electromagnetic radiation is applied utilizing said illumination system having said electromagnetic radiation conveyance device constructed from a transparent material.

14. The method according to claim 13, wherein electromagnetic radiation is applied utilizing said illumination system having said electromagnetic radiation conveyance device constructed from at least one of acrylic, glass, polycarbonate, and polystyrene.

15. The method according to claim 11, wherein electromagnetic radiation is applied utilizing said illumination system having said light directing means said core having a first angle of approximately 45°, wherein said core is configured to reflect electromagnetic radiation toward said left side and said right side.

16. A method of polymerizing a light sensitive material on a dental arch comprising:
  applying said light sensitive material to said dental arch, said light sensitive material is photoreactive, wherein polymerization of said light sensitive material is initiated in response to absorption of electromagnetic radiation; and
  applying electromagnetic radiation to said dental arch utilizing an illumination system comprising:
    the electromagnetic radiation conveyance device of claim 1.

17. The method according to claim 16, wherein electromagnetic radiation is applied utilizing said illumination system, wherein the electromagnetic conveyance device of said illumination system has an electromagnetic radiation emitting device positioned within its proximal end.

18. The method according to claim 16, wherein electromagnetic radiation is applied utilizing said illumination system having said electromagnetic radiation conveyance device constructed from a transparent material.

19. The method according to claim 18, wherein electromagnetic radiation is applied utilizing said illumination system having said electromagnetic radiation conveyance device constructed from at least one of acrylic, glass, polycarbonate, and polystyrene.

20. The method according to claim 16, wherein electromagnetic radiation is applied utilizing said illumination system having said light directing means said core having a first angle of approximately 45°, wherein said core is configured to reflect electromagnetic radiation toward said left side and said right side.

21. An electromagnetic radiation conveyance device comprising:
  a proximal end configured for attachment to an electromagnetic radiation emitting device;
  a distal end anatomically preformed with a profile complementary to a shape of a dental arch; and
  a light directing means comprising a core, a left side, and a right side, wherein said light directing means is intermediate between said proximal end and said distal end, wherein said light directing means is configured to convey electromagnetic radiation from said proximal end to the patient's teeth primarily from the sides and secondarily from several other directions.

* * * * *